Figure 1:
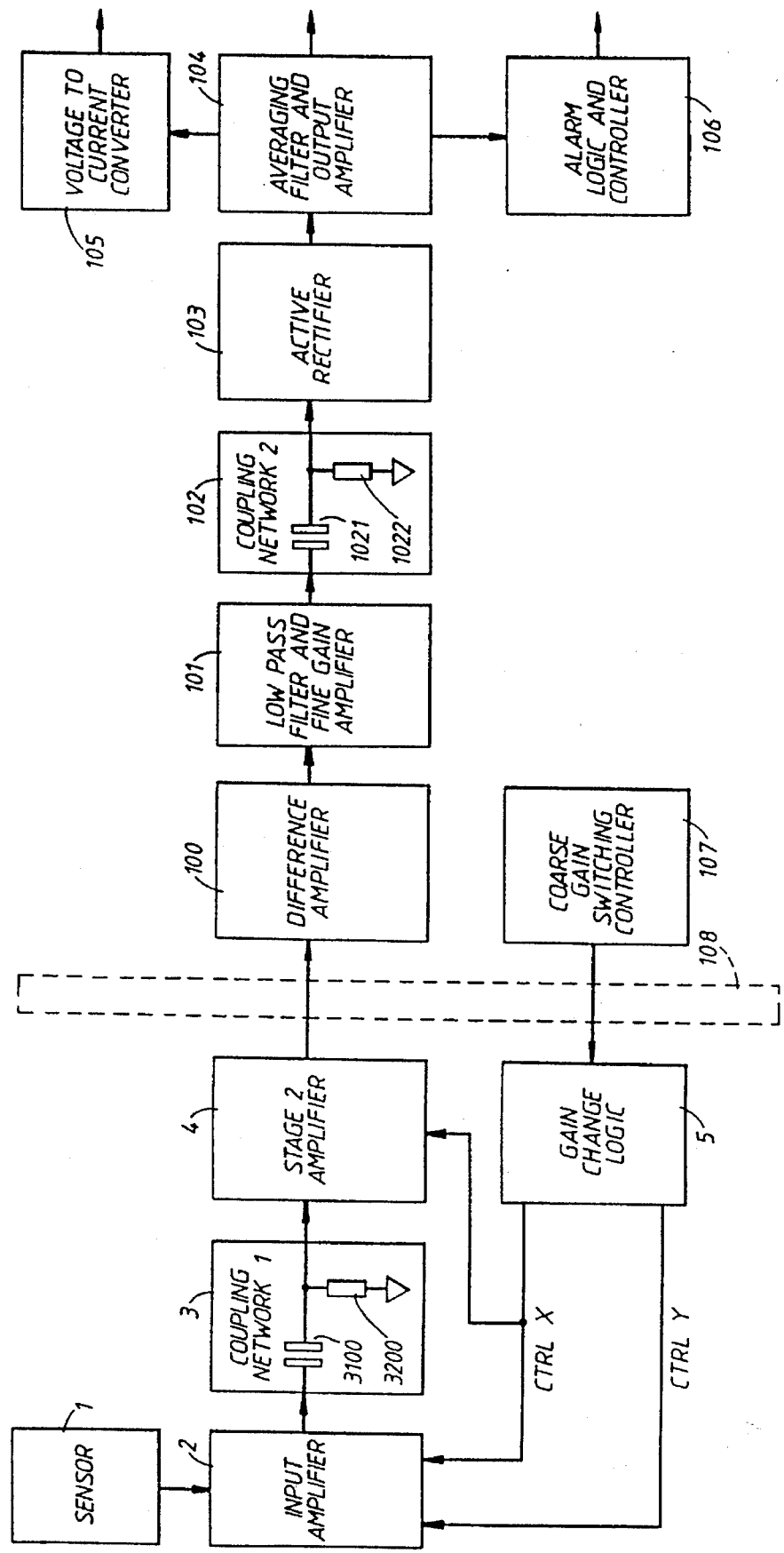

United States Patent [19]
Rigby

[11] Patent Number: 5,591,895
[45] Date of Patent: Jan. 7, 1997

[54] DETECTING PARTICLES IN A GAS FLOW

[75] Inventor: Michael Rigby, Cambridgeshire, Great Britain

[73] Assignee: Pollution Control & Measurement (Europe) Ltd., Huntingdon, Great Britain

[21] Appl. No.: 325,294

[22] PCT Filed: May 5, 1992

[86] PCT No.: PCT/GB92/00816

§ 371 Date: Oct. 31, 1994

§ 102(e) Date: Oct. 31, 1994

[87] PCT Pub. No.: WO93/22653

PCT Pub. Date: Nov. 11, 1993

[30] Foreign Application Priority Data

Apr. 30, 1992 [GB] United Kingdom .................. 9209407

[51] Int. Cl.$^6$ .................................................. G01N 25/00
[52] U.S. Cl. .......................................... 73/28.01; 324/454
[58] Field of Search .......................... 73/28.01; 324/452, 324/454

[56] References Cited

U.S. PATENT DOCUMENTS

| | | |
|---|---|---|
| 3,753,102 | 8/1973 | Beck . |
| 3,813,939 | 6/1974 | Head ............................ 73/194 |
| 3,859,593 | 1/1975 | Poole et al. ..................... 324/32 |
| 3,927,356 | 12/1975 | Hodson et al. .................. 317/123 |
| 3,944,354 | 3/1976 | Benwood et al. ................ 355/3 R |
| 4,041,375 | 8/1977 | Polukshima et al. ............. 324/32 |
| 4,063,154 | 12/1977 | Andrus et al. .................. 324/32 |
| 4,117,715 | 10/1978 | Hoenig ........................... 73/28 |
| 4,179,934 | 12/1979 | Svarovsky . |
| 4,363,244 | 12/1982 | Rabeh et al. ................... 73/861.08 |
| 4,388,588 | 6/1983 | Taylor ............................ 324/72.5 |
| 4,512,200 | 4/1985 | Ghering et al. . |
| 4,607,228 | 8/1986 | Reif . |
| 4,631,482 | 12/1986 | Newton et al. .................. 324/454 |
| 4,714,890 | 12/1987 | Dechene et al. ................ 324/454 |
| 4,904,944 | 2/1990 | Dechene et al. . |
| 5,022,274 | 6/1991 | Klinzing et al. ................. 73/861.04 |
| 5,054,325 | 10/1991 | Dechene et al. . |
| 5,055,794 | 10/1991 | Kawashima ..................... 324/453 |
| 5,095,275 | 3/1992 | Dechene et al. ................ 324/454 |
| 5,287,061 | 2/1994 | Dechene et al. ................ 324/454 |
| 5,396,806 | 3/1995 | Dechene et al. ................ 73/861.04 |

FOREIGN PATENT DOCUMENTS

| | | |
|---|---|---|
| 0110802A3 | 6/1984 | European Pat. Off. . |
| 0144193A2 | 6/1985 | European Pat. Off. . |
| 0256845A2 | 2/1988 | European Pat. Off. . |
| 2215608 | 8/1974 | France . |
| 1195960 | 7/1965 | Germany . |
| 62-003621 | 1/1987 | Japan . |
| 62-003622 | 1/1987 | Japan . |
| 1485750 | 9/1977 | United Kingdom . |
| 1578157 | 11/1980 | United Kingdom . |
| 2121542 | 12/1983 | United Kingdom . |
| 2166874 | 5/1986 | United Kingdom . |
| WO86/02453 | 4/1986 | WIPO . |

Primary Examiner—Hezron E. Williams
Assistant Examiner—Jay I. Politzer
Attorney, Agent, or Firm—Kane, Dalsimer, Sullivan, Kurucz, Levy, Eisele and Richard, LLP

[57] ABSTRACT

In a method for detecting particles in a gas flow, a probe 8 is charged triboelectrically by particles 10 in the flow and the quantities of electrical charges transferred to the probe are evaluated to provide an indication of the particle flow in the gas flow. In order to reduce the effect of variations in "gas flow related variables" other than those relating to particle flow, an alternating component in the signal caused by the triboelectrical charging of the probe is monitored.

8 Claims, 5 Drawing Sheets

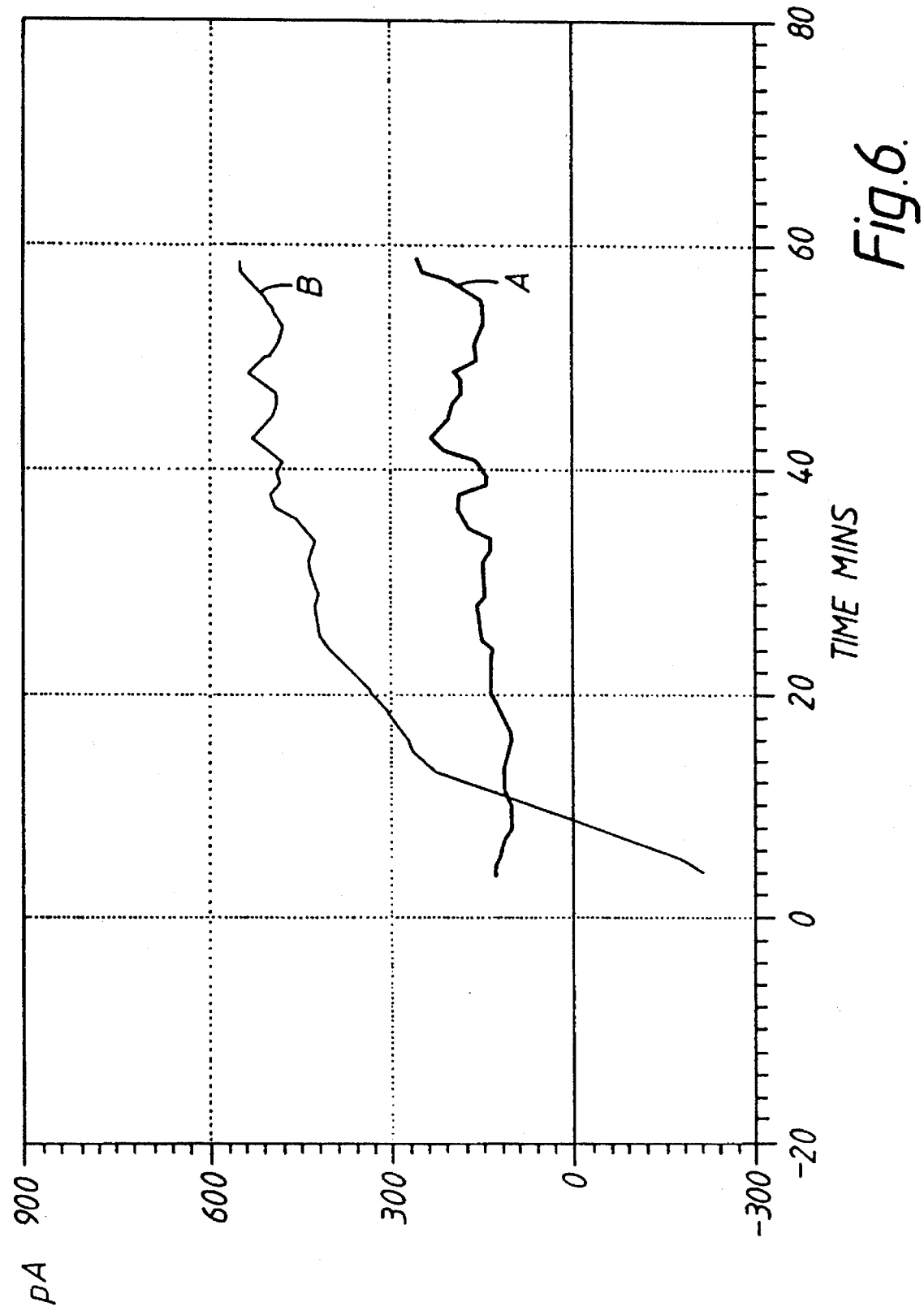

DETECTING PARTICLES IN A GAS FLOW

This invention relates to an apparatus and method for detecting particles in a gas flow. The invention is particularly concerned with an arrangement in which particles are detected as a result of those particles triboelectrically charging a probe in a duct along which a gas flows.

WO 86/02454 describes an apparatus which uses triboelectric effects. A metal probe projects into a duct and particles carried past the probe in the gas flow impart triboelectric charges to the probe. Those charges are conducted to ground through an electric circuit, resulting in an electric current. The current is converted to a unipolar voltage and amplified to provide an indication of the mass of the particles.

In WO 86/02454 an auto-zero circuit is preferably provided to rezero the circuit periodically (about once per minute) in order to prevent the output of the circuit varying with ambient temperature as a result of changing electrical characteristics of the current to voltage conversion circuit. As an alternative to the auto-zero circuit a system which uses only the a.c. component of the signal can be used apparently for the same purpose. In commercial versions of the apparatus described in WO 86/02454, the auto-zero circuit is employed.

We have found that apparatus of the kind described in WO 86/02454 is unable to give a reliable indication of the mass flow rate of particles in the gas flow and that the magnitude of the current generated by the charges is influenced by factors other than the mass of the particles.

It is an object of the invention to provide a method and apparatus for detecting particles in a gas flow which relies upon particles in the flow triboelectrically charging a probe and which is less affected by changes in other variables relating to the gas flow.

According to the invention there is provided a method for detecting particles in a gas flow in which a probe is charged triboelectrically by particles in the flow and the quantities of electrical charges transferred to the probe are evaluated to provide an indication of the particle flow in the gas flow, wherein, in order to reduce the effect of variations in "gas flow related variables" other than those relating to particle flow, an alternating component in the signal caused by the triboelectrical charging of the probe is monitored. The term "gas flow related variables" refers to variables that are related to the environment in the region of the gas flow and at the probe, to the gas flow itself and/or to the particles in the gas flow. Examples of gas flow related variables other than those relating to particle flow are therefore: humidity in the region of the gas flow, temperature of the gas flow, thickness of a particulate layer deposited on the probe, and the electrical charge of particles in the gas flow. Examples of gas flow related variables that relate to particle flow are the mass flow rate of the particles, and the velocity and size of the particles.

We have discovered that by looking at the alternating component in the signal from the triboelectrically charged probe rather than looking at the absolute value of that signal, it is possible to obtain an output signal that is much less affected by gas flow related variables, other than those relating to particle flow, than in the case of, for example, the apparatus described in WO 86/02454. Although it might appear to be disadvantageous to evaluate the much smaller amplitude alternating signal component involved, we have found that such disadvantages are more than compensated for by the much improved correlation between, for example, the mass flow rate of particles in the flow and the alternating component in the signal from the probe. More particularly, we have found that whereas variations in gas flow related variables other than those relating to particle flow are liable to affect the absolute value of a signal from a probe charged triboelectrically, they are not likely to affect the magnitude of the alternating component of the signal to the same extent. This hitherto undiscovered phenomenon is not fully understood but it is believed that factors such as humidity, electrical charges already on the particles and a build-up of particles on the probe all affect the absolute value of the current without affecting the alternating component of the current as much.

Preferably the alternating component of the signal from the probe is filtered to limit the frequency to below about 2 Hz, preferably about 1.5 Hz. By eliminating higher frequencies the risk of spurious signals derived from mechanical vibration of the probe is substantially reduced since the resonant frequency of such vibration is likely to be substantially higher than 2 Hz.

Preferably the alternating component of the signal from the probe is filtered to limit the frequency of the signal to above about 0.1 Hz, preferably about 0.15 Hz. By eliminating lower frequencies the risk of spurious signals derived from transient temperature-generated voltages is substantially reduced.

Preferably the alternating component of the signal from the probe is amplified in a plurality of stages. In that case low frequencies, which may be those below 0.15 Hz, are preferably attenuated at the first stage of amplification.

In the most common case, the size and composition of the particles will not vary and the flow will be monitored in order to detect variations in the mass flow rate. Given that the size of the particles and their composition does not vary, the measurement of mass flow rate can alternatively be regarded as a measurement of the flow rate in terms of the number of particles per unit time.

Usually it will be desired to provide a quantitative indication of the mass flow rate but for some applications it may be adequate simply to provide an indication of whether or not the mass flow rate measured is above or below some threshold level. An alarm may be sounded if the mass flow rate is above the threshold level.

Usually, the gas flow is along a duct and the probe is in the duct.

The present invention also provides the use, in an apparatus for detecting particles in a gas flow, which apparatus includes a probe for installation in the gas flow, of an electric circuit for generating an electric signal from electrical charges transferred to the probe as a result of triboelectric charging thereof by particles in the flow, and evaluating means for providing an output signal in dependence upon an alternating component of the electric signal generated in the circuit, as a means for reducing the effect of variations in "gas flow related variables" other than those relating to particle flow.

The invention can be used for continuous measurement of mass flow rate of particles in applications where particles are suspended in a gas flow. Examples of applications are: continuous measurement of unwanted particulate emissions from stacks and dust arrestment plants and continuous measurement of particle mass flow rates in systems where particles are suspended in a gas stream, for example in a pneumatic conveying system.

Figure 2:
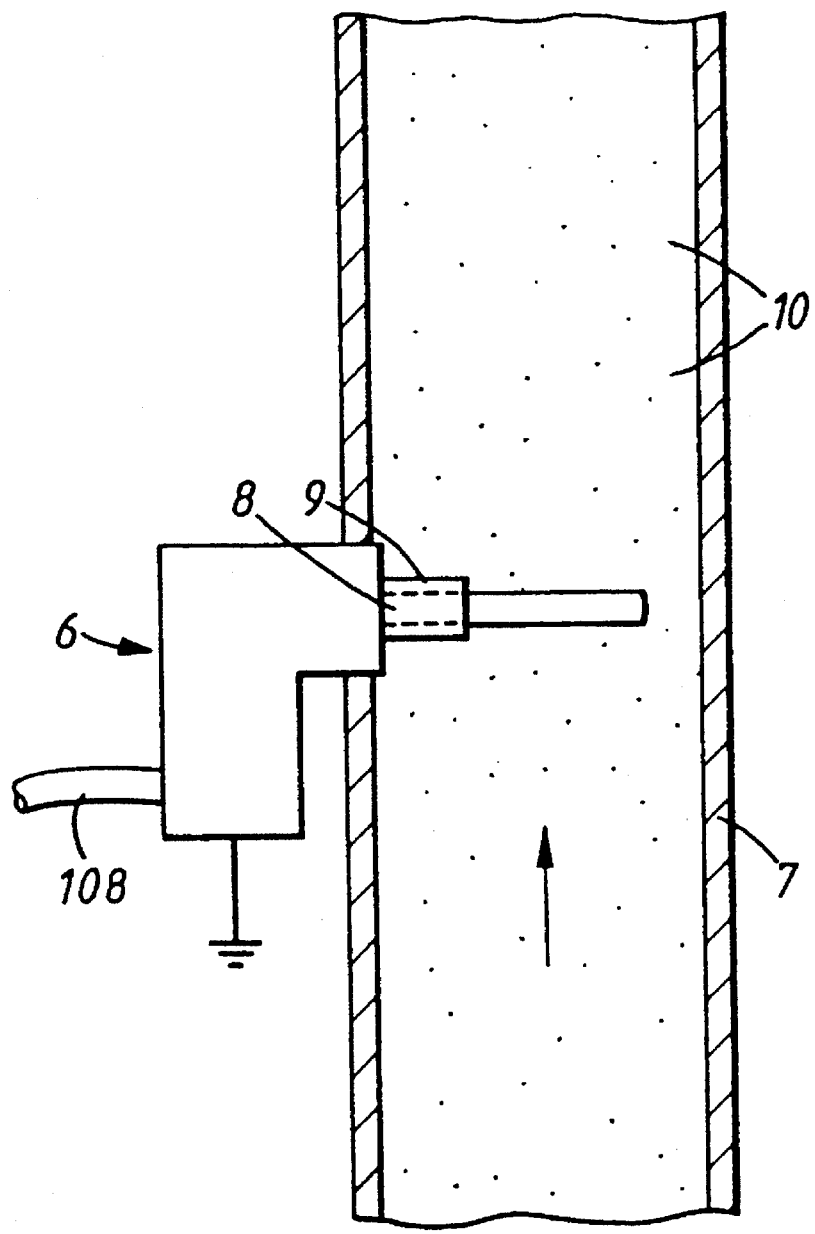
Figure 3:
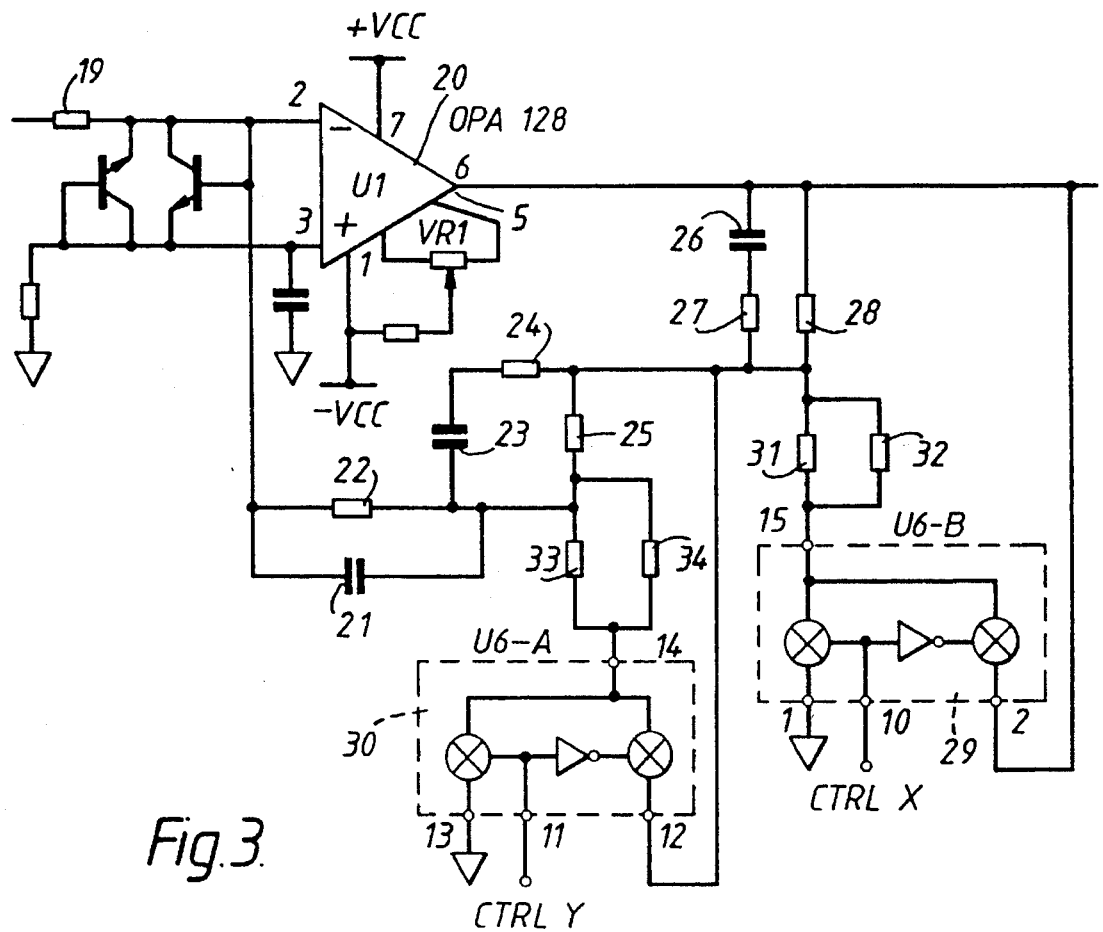
Figure 4:
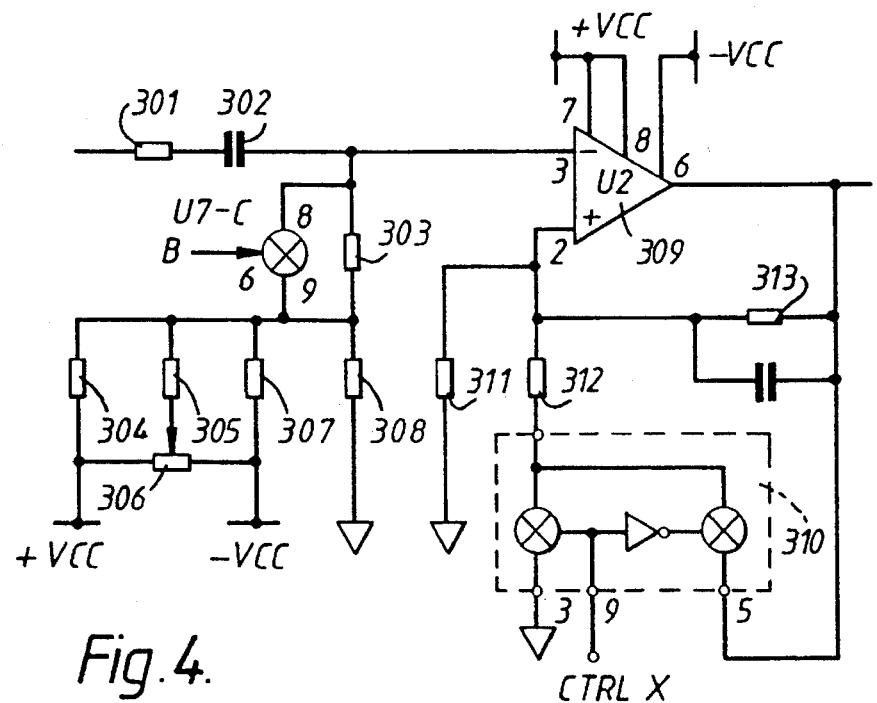
Figure 5A:
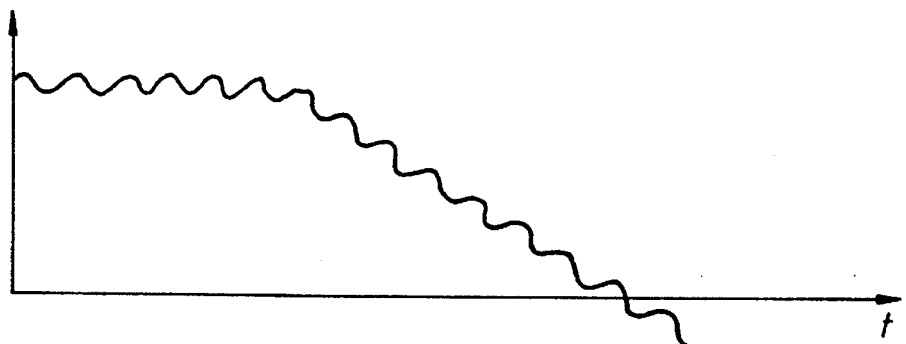
Figure 5B:
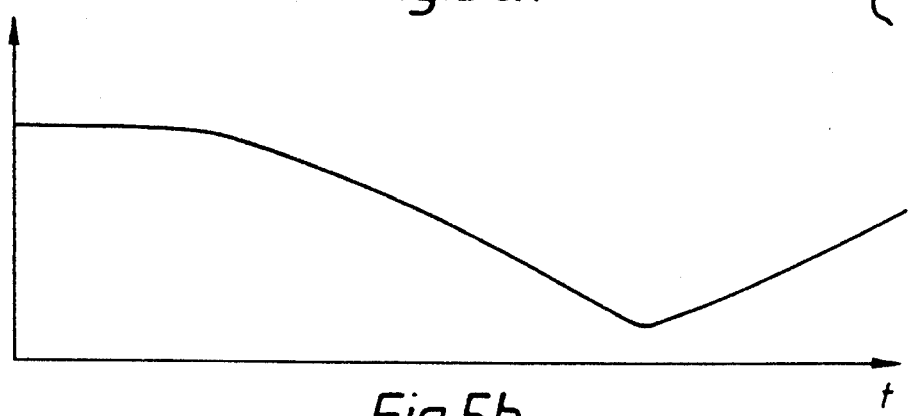
Figure 5C:
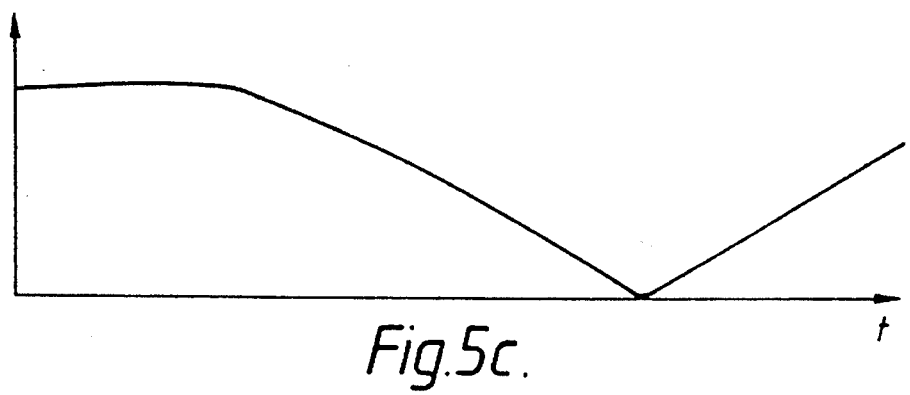
Figure 5D:
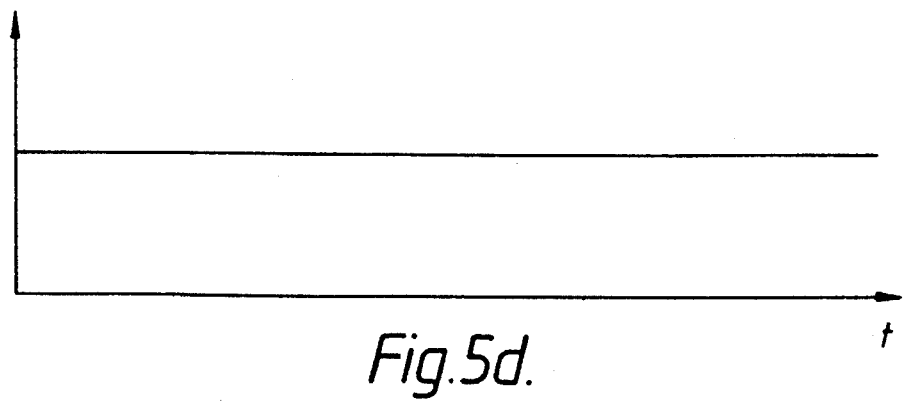

Dust flow monitoring apparatus in accordance with the invention will now be described by way of example only with reference to the accompanying drawings, in which:

FIG. 1 is a block-diagram representation of the electrical system of the dust flow monitoring apparatus, FIG. 2 is a schematic sectional view of a sensing head mounted on a stack along which dust-carrying air is passing, FIG. 3 is a circuit-diagram representation of an input amplifier forming a part of the electrical system, FIG. 4 is a circuit-diagram representation of a coupling network and a second stage amplifier forming another part of the electrical system, FIG. 5a is a graph of the current from the probe plotted against time in a case where the particle flow remains constant but other variables in the duct alter, FIGS. 5b to 5d are graphs of signal amplitude against time for different signals that can be derived from the current signal of FIG. 5a, and FIG. 6 is a graph showing the a.c. and d.c. current outputs from a probe monitoring an air flow to which coal particles are added at a constant rate.

Referring to FIG. 1 of the accompanying drawings, the electrical system of the dust flow monitoring apparatus includes a sensor 1, an input amplifier 2, a first coupling network 3, a second stage amplifier 4, a gain-change logic circuit 5, a difference amplifier 100, a low-pass filter and fine-gain amplifier 101, a second coupling network 102, an active rectifier 103, an averaging filter and output amplifier 104, a voltage-to-current converter 105, an alarm logic and controller 106, and a coarse gain switching controller 107.

The sensor 1, the input amplifier 2, the first coupling network 5 and the second stage amplifier 4 are connected in cascade. The gain-change logic circuit 5 has a first connection connected to the input amplifier 2 and to the second stage amplifier 4, and a second connection connected only to the input amplifier 2. The coarse gain switching controller 107 is connected to the gain-change logic circuit 5.

The difference amplifier 100, the low-pass filter and fine-gain amplifier 101, the second coupling network 102, the active rectifier 103 and the averaging filter and output amplifier 104 are connected in cascade. The voltage-to-current converter 105 and the alarm logic and controller 106 are connected to the averaging filter and output amplifier 104.

Referring now also to FIG. 2 the sensor 1, the input amplifier 2, the first coupling network 3, the second stage amplifier 4 and the gain-change logic circuit 5 form a sensing head 6 which, in use, is mounted on a stack 7, the dust flow along which is being monitored. The remainder of the electrical system is "control room" equipment and is located at a position remote from the sensing head. The second stage amplifier 4 of the sensing head 6 is connected to the difference amplifier 100 of the "control room" equipment by way of a connection means 108 which might include a length of cable. The gain-change logic circuit 5 is connected to the coarse gain switching controller 107 by way of the connection means 108.

The sensor 1 includes a conducting rod 8 forming a probe which projects into the stack. The conducting rod 8 is covered by an insulating member 9 which may be of a ceramic or PTFE material and the insulating member 9 extends some of the way along the conducting rod 8 towards its free end but stops short of the end.

The input amplifier 2 is a shunt-feedback current amplifier which converts its input current, which is the current supplied by the conducting rod, into an output voltage. The amplifier 2 is d.c. coupled and has switchable components providing selectable transimpedance gains of between 0.1 millivolts per picoampere and 40 millivolts per picoampere in four steps. The four steps provide transimpedance gains of 0.1 millivolts per picoampere, 0.4 millivolts per picoampere, 10 millivolts per picoampere and 40 millivolts per picoampere, respectively. The input amplifier 2 also includes capacitance resistance feedback networks which set the upper frequency response at about 1.5 Hz.

The output signal from the input amplifier 2 passes to the first coupling network 3 which includes a series capacitor 3100 and shunt resistor 3200. The series capacitor 3100 blocks the d.c. and very low frequency signals from the input amplifier 2, the capacitor 3100 and resistor 3200 being selected to set the lower frequency response of the signal path at 0.15 Hz.

The signal passing through the capacitor 3100 next goes to the second stage amplifier 4 which is a d.c. coupled voltage amplifier having switchable gain-setting means for setting its gain to 2 or to 5.

The gain switching arrangements of the amplifiers 2 and 4 are so linked as to provide overall transimpedance gains of 0.2 millivolts per picoampere, 2 millivolts per picoampere, 20 millivolts per picoampere and 200 millivolts per picoampere, respectively.

The settings of the transimpedance-gain of the input amplifier 2 and the voltage gain of the second stage amplifier 4 are effected by the gain-change logic circuit 5 operating under the control of the coarse gain switching controller 107 which is controlled manually.

The selected maximum transimpedance gain of the input amplifier 2 provides a good signal-to-noise ratio for the system by ensuring that a significant proportion of the required system gain is provided at the input stage without raising significant difficulties of temperature-generated output voltage. The potential difficulty of temperature-generated output voltage is also met by limiting the lower frequency of the transmission path to 0.15 Hz by means of the first coupling network 3. The selection of the upper frequency limit as 1.5 Hz is effective to counter the effects of mechanical vibration and noise while providing a bandwidth adequate for providing accurate information on the flow rate of dust particles impinging on the sensor 1. That is, the system bandwidth is carefully selected in order to counter a range of system effects which generate signals likely to cause errors in the final result. Other turn-over frequencies may be used at the cost of reduced effectiveness of the system in discriminating against unwanted effects.

The bandwidth-limited output signal from the second stage amplifier 4 passes to the difference amplifier 100 where it is subjected to additional bandwidth-shaping by means of capacitor-resistor networks in order to improve the high-frequency roll off above 1.5 Hz. The difference amplifier 100 is a differential amplifier and has a high common-mode rejection ratio. The capacitor-resistor networks include a parallel capacitor-resistor network shunting the non-inverting input terminal of the amplifier and another parallel capacitor-resistor network connected between the inverting input terminal of the amplifier and its output terminal.

The signal next passes to the low-pass filter and fine-gain amplifier 101 where further low-pass characteristic shaping is applied by means of capacitance-resistance networks which provide a 12 bB/octave roll-off above 1.5 Hz. The low-pass filter and fine-gain amplifier also provides continuously adjustable voltage gain of between 1 and 10. The capacitor-resistor networks include two resistors connected in series with each other and with the non-inverting terminal of the amplifier, a capacitor connected between the junction of the two resistors and the inverting terminal of the amplifier, and a further capacitor connected between the non-inverting terminal of the amplifier and a grounding point of the system.

The second coupling network 102 receives the signal from the low-pass filter and fine-gain control amplifier 101. The second coupling network 102 has a series capacitor 1021 and a shunt resistor 1022 and serves to block temperature-generated signals and time-dependent d.c. signals introduced after the first coupling network 3.

The signals passing through the coupling network 102 go to the active rectifier 103 which also provides a voltage gain of 2. The signals then pass to the averaging filter and output amplifier 104 which provides a long-term average of the signals, reducing the random signal variations which particle flow provides. The averaging filter and output amplifier also provides a voltage gain of 5.

The averaging filter and amplifier 104 provides signals for a voltage-to-current converter 105 for driving a pen-recorder or the like. The voltage-to-current converter is capable of providing a 4 to 20 mA output current swing for an input voltage swing of 0 to 10 volts. The averaging filter and amplifier 104 also provides an output of range 0 to 10 volts.

A signal from the averaging filter and output amplifier 104 is applied to the alarm logic and controller 106 which is set to trigger when a set level is exceeded. There is also an arrangement for setting the alarm logic and controller 106 to trigger when the applied signal falls below a set threshold.

Referring to FIG. 3 of the accompanying drawings, the principal components of the input amplifier are a differential-input operational amplifier 20, a third capacitor-resistor network consisting of a capacitor 21 in parallel with a resistor 22, a fourth capacitor-resistor network consisting of a series-connected capacitor 23 and resistor 24 in parallel with a resistor 25, a fifth capacitor-resistor network consisting of a series-connected capacitor 26 and resistor 27 in parallel with a resistor 28, two transmission gate switches 29 and 30, and resistors 19, 31, 32, 33 and 34.

The resistor 19 is connected in series with the inverting input terminal of the operational amplifier 20. The third, fourth and fifth capacitor-resistor networks are connected in series with one another in that order between the inverting input terminal of the operational amplifier 20 and its output terminal. The resistors 31 and 32 are connected in parallel with each other and connect the junction of the fourth and fifth capacitor-resistor networks to a first terminal of the transmission gate switch 29. A second terminal of the transmission gate switch 29 is connected to the system ground and a third terminal of the switch is connected to the output terminal of the operational amplifier 20. The resistors 33 and 34 are connected in parallel with each other and connect the junction of the third and fourth capacitor-resistor networks to a first terminal of the transmission gate switch 30. A second terminal of the transmission gate switch 30 is connected to the system ground and a third terminal of the switch is connected to the junction between the fourth and fifth capacitor-resistor networks.

The transmission gate switch 30 is controlled by a logic signal CTRL Y. When the signal CTRL Y is high, the first terminal of the transmission gate switch 30 is connected to its second terminal and when the signal CTRL Y is low, the first terminal of the switch is connected to its third terminal. The transmission gate switch 30, therefore, is operable either to connect the resistors 33 and 34 to the system ground (CTRL Y high) or to connect those resistors to the junction between the fourth and fifth capacitor-resistor networks (CTRL Y low), that is, in parallel with the resistor 25.

The transmission gate switch 29 is controlled by a logic signal CTRL X. When the signal CTRL X is high, the first terminal of the transmission gate switch 29 is connected to its second terminal and, when the signal CTRL X is low, the first terminal of the switch is connected to its third terminal. The transmission gate switch 29, therefore, is operable to connect the resistors 31 and 32 to the system ground (CTRL X high) or to connect those resistors to the output terminal of the operational amplifier 20.

The transmission gate switches 29 and 30 set the overall gain of transimpedance amplifier 20 to one of four possible values as follows:

CTRL X low, CTRL Y low: gain is 0.1 mV/pA
CTRL X low, CTRL Y high: gain is 0.4 mV/pA
CTRL X high, CTRL Y low: gain is 10 mV/pA
CTRL X high, CTRL Y high: gain is 40 mV/pA The logic signals CTRL X and CTRL Y are generated by the gain-change logic circuit 5 shown in FIG. 1.

Referring to FIG. 4 of the accompanying drawings, the principal components of the coupling network and second stage amplifier are resistors 301 and 303 to 308, a capacitor 302, a differential-input operational amplifier 309, a transmission gate switch 310, and resistors 311, 312 and 313.

The capacitor 302 is connected in series with the non-inverting input terminal of the operational amplifier 309, the resistor 301 is connected in series with the capacitor 302. The resistors 303 and 308 shunt the non-inverting input terminal of the operational amplifier 309 to a ground terminal. The resistors 304 and 307 are not normally fitted; one or other may be fitted as required to increase the range of the potentiometer 306. The potentiometer 306 and the resistors 305 and 308 serve to adjust and possibly remove the input offset voltage of the second-stage amplifier 309.

The capacitor 302 and the resistor 303 serve as the dominant elements of the coupling network connected to the non-inverting input terminal of the operational amplifier 309. The capacitor 302 serves to block d.c. signals but is large enough to permit signals of 0.15 Hz and above to pass. The capacitor 302 may have a value of the order of 0.5 µF. The capacitor 302 and the resistor 303, the value of which is of the order of 2 MΩ contribute towards setting the lower break frequency for the amplifier system at about 0.15 Hz.

The resistors 311, 312 and 313 form a network which defines the voltage gain of the second-stage amplifier 309. The resistor 313 is connected between the inverting input and the output of the amplifier 309. The resistor 311 is connected between the inverting input of the amplifier 309 and the system ground. The resistor 312 is connected between the common terminal of the transmission gate switch 310 and the inverting input of the amplifier 309 so that when the signal CTRL X is high, the resistor 312 is connected to the system ground, and when the signal CTRL X is low, the resistor 312 is connected to the output of the amplifier 309. When the signal CTRL X is high, the gain of amplifier 309 is five, and when the signal CTRL X is low, the gain of the amplifier is two.

Since the signal CTRL X controls the transmission gate switches 29 and 310, the gains of the input amplifier 20 and the second-stage amplifier 309 are switched together. That provides selectable overall gains from the input of amplifier 20 to the output of the amplifier 309 of 0.2 mV/pA, 2 mV/pA, 20 mV/pA and 200 mV/pA.

We have found that by processing the signal as described above an output that provides an accurate indication of particle mass flow rate (for constant particle size, material and velocity) can be obtained and, especially, we have found that in practice a much more accurate indication is obtained by processing the alternating component of the signal rather than the absolute level of the signal. The difference in the two techniques is shown qualitatively in FIGS. 5a to 5d. FIG. 5a shows one form of current signal that we have found can be produced from a probe when the average mass flow rate of particles is constant. It will be noted that the signal starts with a current which has a large d.c. component of amplitude a and a relatively small a.c. component of amplitude b. With the passage of time, however, variables in the duct change: perhaps the humidity of the gas flow changes, perhaps there is a build-up of charged particles on the probe or perhaps a static charge on the particles upstream of the probe changes; as a result, the d.c. component of the current reduces or even, as shown in FIG. 5a, changes in polarity, but the smaller a.c. component remains relatively constant. FIG. 5b shows the output signal that is obtained from monitoring the absolute value of the current, including the alternating component, and then rectifying the output, that being the procedure adopted in the preferred embodiment of WO 86/02454. FIG. 5c shows the output signal that is obtained from monitoring the absolute value of the current, excluding the alternating component, and then rectifying the output. FIG. 5d shows the output signal that is obtained from monitoring the amplitude of the alternating component of the current in accordance with the invention. It will readily be seen that the output signals of FIGS. 5b and 5c suggest that the mass flow rate of particles is changing, whereas the output signal of FIG. 5d correctly indicates a constant mass flow rate of particles. The variation in the d.c. component of the current is caused by variations in variables in the duct other than those related to the particle mass flow rate, particle size or particle velocity.

FIG. 6 shows the results, in the form of current in picoamperes plotted against time in minutes, of an experiment carried out to compare the results of monitoring the a.c. and d.c. components of current in the signal from the probe. In the experiment coal dust particles of substantially constant size were added at a substantially constant rate, of the order of 500 mg m$^{-3}$ to an air flow of 25 m s$^{-1}$. In FIG. 6 plot A shows the a.c. component of the probe current and plot B shows the d.c. component. It can be seen that although the particle flow rate is substantially constant, the d.c. signal alters radically, even changing polarity whereas the a.c. signal gives a much more consistent output.

I claim:

1. A method for detecting particles flowing in a gas flow along a stack and emitted through the stack in which a probe is positioned so that it projects into the flow of particles in the stack and is charged triboelectrically by particles in the flow and the quantities of electrical charges transferred to the probe are evaluated to provide an indication of the particle flow in the gas flow, wherein, in order to reduce the effect of variations in gas flow related variables other than those relating to particle flow, an alternating component in the signal caused by the triboelectrical charging of the probe is monitored, the alternating component of the signal from the probe is filtered to exclude high frequency components of the signal and the magnitude of the residual alternating component is itself used to give an indication of the particle flow through the stack.

2. A method according to claim 1 in which the alternating component of the signal from the probe is filtered to limit the frequency to below about 2 Hz.

3. A method according to claim 2 in which the alternating component of the signal from the probe filtered to limit the frequency to below about 1.5 Hz.

4. A method according to claim 1 in which the alternating component of the signal from the probe filtered to limit the frequency to above about 0.1 Hz.

5. A method according to claim 4 in which the alternating component of the signal from the probe is filtered to limit the frequency to above about 0.15 Hz.

6. A method according to claim 1 in which the alternating component of the signal from the probe is amplified in a plurality of stages.

7. A method according to claim 6 in which frequencies below about 0.15 Hz are attenuated at the first stage of amplification.

8. An apparatus for detecting particles in a gas flow along a stack and emitted through the stack, the apparatus including a probe for installation in the gas flow, an electric circuit for generating an electric signal from electrical charges transferred to the probe as a result of triboelectric charging thereof by particles in the gas flow, and evaluating means for providing an output signal in dependence upon the electric signal generated in the circuit, wherein the apparatus is used to reduce the effect of variations in gas flow related variables other than those relating to particle flow, the electric signal that is generated by the circuit has an alternating component and the evaluating means is arranged to provide an output in dependence upon the magnitude of the alternating component of the electric signal after filtering and comprises filter means to filter the alternating component of the signal to exclude high frequency components of the signal.

\* \* \* \* \*